(12) United States Patent
Cho et al.

(10) Patent No.: US 11,609,161 B2
(45) Date of Patent: *Mar. 21, 2023

(54) PISTON OF NUCLEIC ACID EXTRACTING CARTRIDGE

(71) Applicant: SD BIOSENSOR, INC., Suwon-si (KR)

(72) Inventors: Young Shik Cho, Yongin-si (KR); Hyo Guen Lee, Suwon-si (KR); Hae Joon Park, Seongnam-si (KR); Sun Young Lee, Suwon-si (KR); Kwan Hun Lim, Suwon-si (KR); In Ae Kim, Gwangmyeong-si (KR); Jae Young Kim, Suwon-si (KR); Hyo Lim Park, Suwon-si (KR); Dong Hun Kim, Suwon-si (KR)

(*) Notice: Subject to any disclaimer, the term of this patent is extended or adjusted under 35 U.S.C. 154(b) by 201 days.

This patent is subject to a terminal disclaimer.

(21) Appl. No.: 16/956,586

(22) PCT Filed: Dec. 20, 2018

(86) PCT No.: PCT/KR2018/016306
§ 371 (c)(1),
(2) Date: Jun. 20, 2020

(87) PCT Pub. No.: WO2019/132404
PCT Pub. Date: Jul. 4, 2019

(65) Prior Publication Data
US 2021/0285853 A1 Sep. 16, 2021

(30) Foreign Application Priority Data

Dec. 28, 2017 (KR) .................. 10-2017-0182629

(51) Int. Cl.
*G01N 1/34* (2006.01)
*G01N 35/02* (2006.01)
(Continued)

(52) U.S. Cl.
CPC ............. *G01N 1/34* (2013.01); *G01N 1/4044* (2013.01); *G01N 35/026* (2013.01); *G01N 35/04* (2013.01);
(Continued)

(58) Field of Classification Search
CPC ...... G01N 1/34; G01N 1/4044; G01N 35/026; G01N 35/04; G01N 35/1009;
(Continued)

(56) References Cited

U.S. PATENT DOCUMENTS 6,374,684 B1 * 4/2002 Dority ................ G01N 35/1097
73/864.81
7,217,513 B2 * 5/2007 Parameswaran ...... B01L 3/0282
435/6.16
(Continued)

FOREIGN PATENT DOCUMENTS

| JP | 2004-191364 | 7/2004 |
| JP | 2010-190907 | 9/2010 |
| KR | 10-1642434 | 7/2016 |

OTHER PUBLICATIONS

Office Action issued by the JPO dated May 10, 2022.

*Primary Examiner* — Marrit Eyassu
(74) *Attorney, Agent, or Firm* — Harvest IP Law LLP

(57) ABSTRACT

There is provided a piston of a cartridge for extracting nucleic acids comprising: a cylindrical upper body having a hollow; a lower body having two ports; a control rod module combined to the other end of the upper body to seal the other end and move up and down along the hollow; and a rotation control module that is combined to the shaft of the lower body to transmit a driving force to the lower body.

9 Claims, 5 Drawing Sheets

(51) Int. Cl.
*G01N 35/04* (2006.01)
*G01N 35/10* (2006.01)
*G01N 35/00* (2006.01)
*G01N 1/40* (2006.01)

(52) U.S. Cl.
CPC ............ G01N 35/1009 (2013.01); *G01N 2035/00326* (2013.01); *G01N 2035/00475* (2013.01); *G01N 2035/00534* (2013.01); *G01N 2035/0429* (2013.01); *G01N 2035/1034* (2013.01)

(58) Field of Classification Search
CPC .......... G01N 2035/00326; G01N 2035/00475; G01N 2035/00534; G01N 2035/0429; G01N 2035/1034; G01N 2035/00465; B01L 3/527; B01L 2300/0681; B01L 2400/0478; B01L 2400/0644; B01L 3/502; C12N 15/1017
USPC .......................................... 436/178
See application file for complete search history.

(56) References Cited

U.S. PATENT DOCUMENTS

| | | | | |
|---|---|---|---|---|
| 7,674,581 B1* | 3/2010 | Fries | ............ | G01N 1/02 |
| | | | | 422/68.1 |
| 7,988,935 B2* | 8/2011 | Yuan | ............ | G01N 1/14 |
| | | | | 422/534 |
| 8,062,846 B2* | 11/2011 | Bortolin | ............ | B01L 3/502 |
| | | | | 422/537 |
| 2015/0209789 A1* | 7/2015 | Kho | ............ | B01L 3/523 |
| | | | | 435/287.2 |

* cited by examiner

[Fig.1]
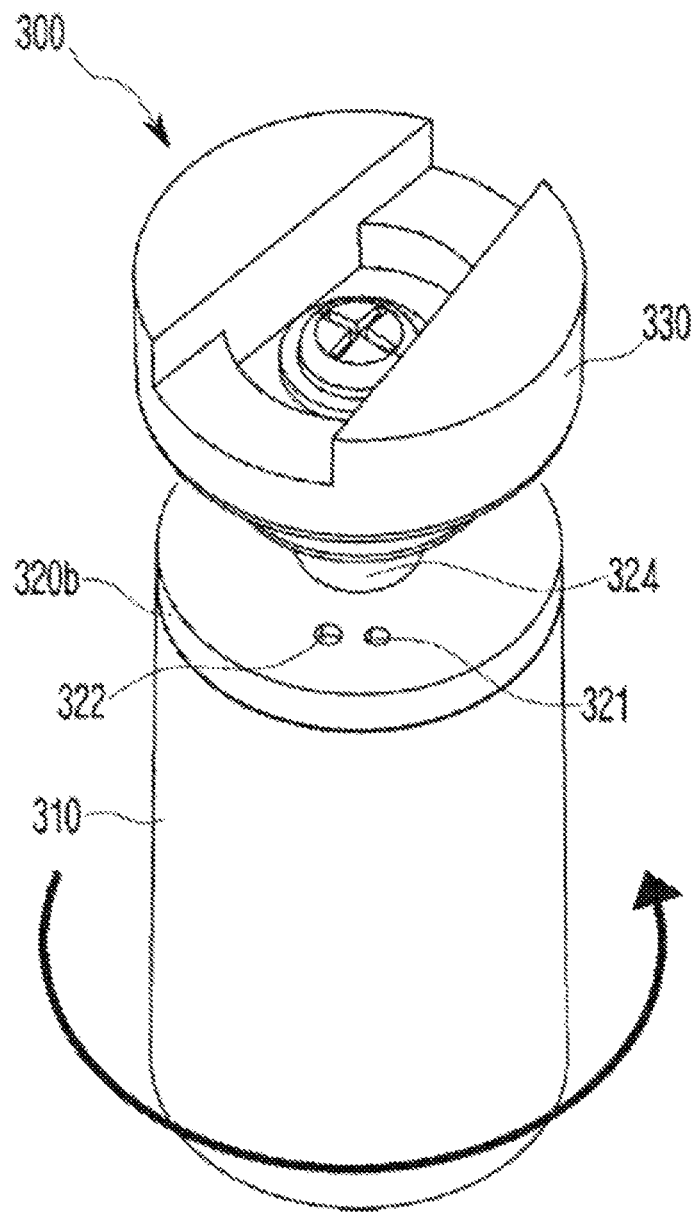

[Fig. 2]
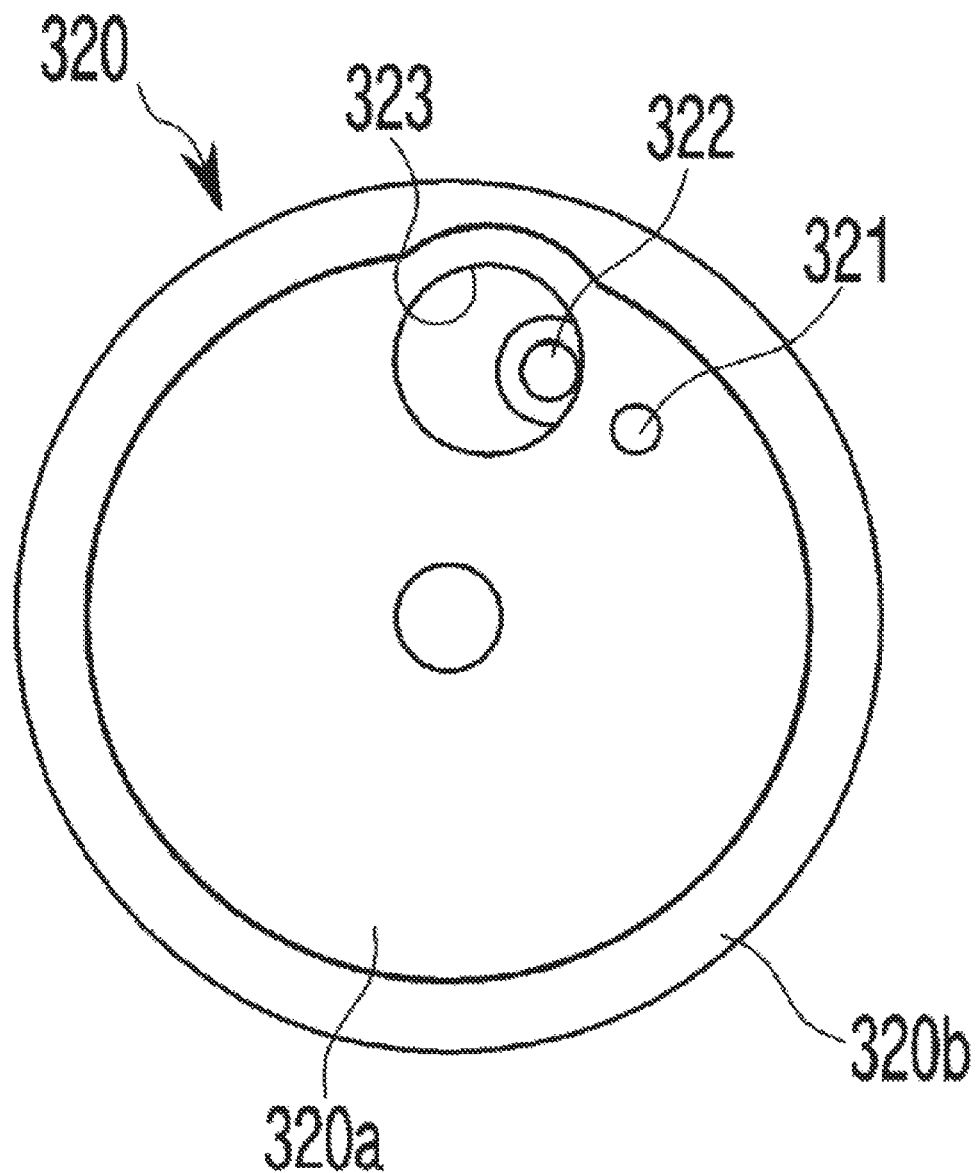

[Fig. 3]
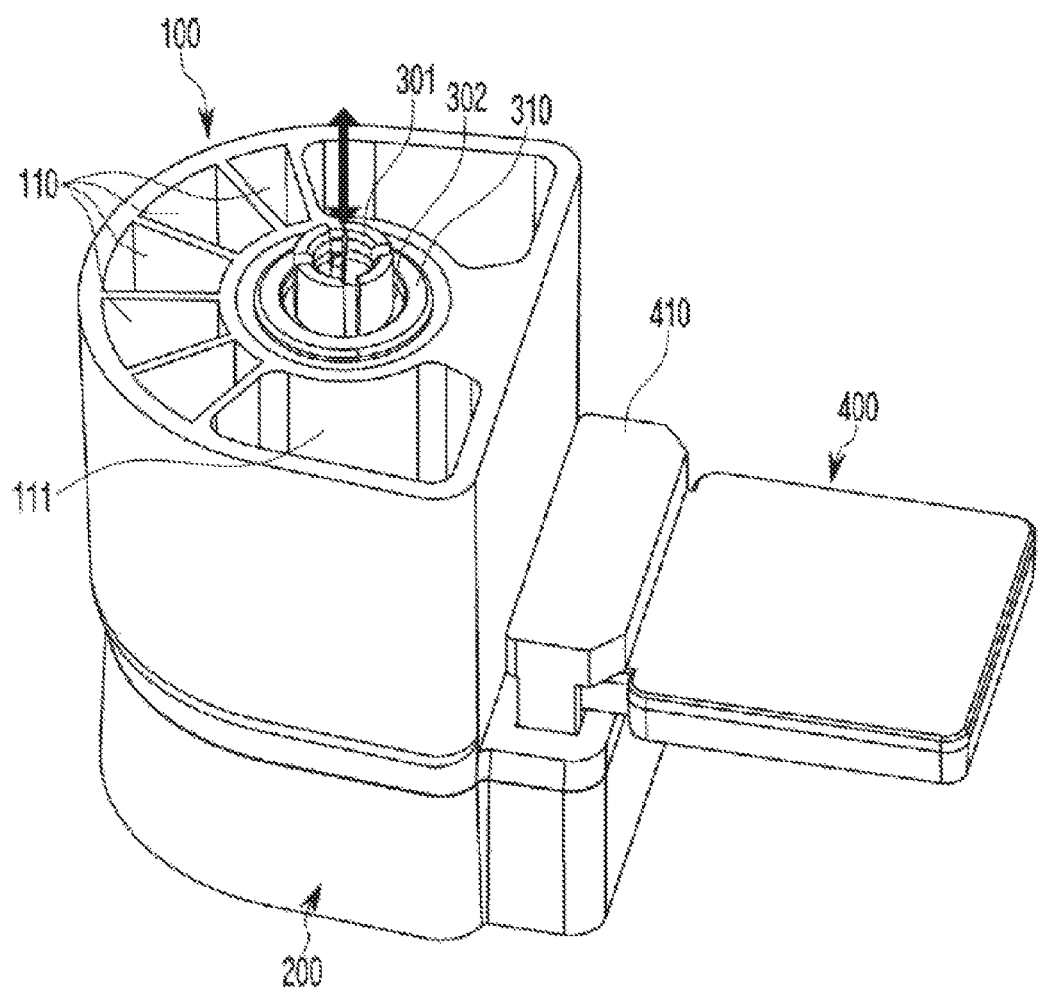

[Fig.4]
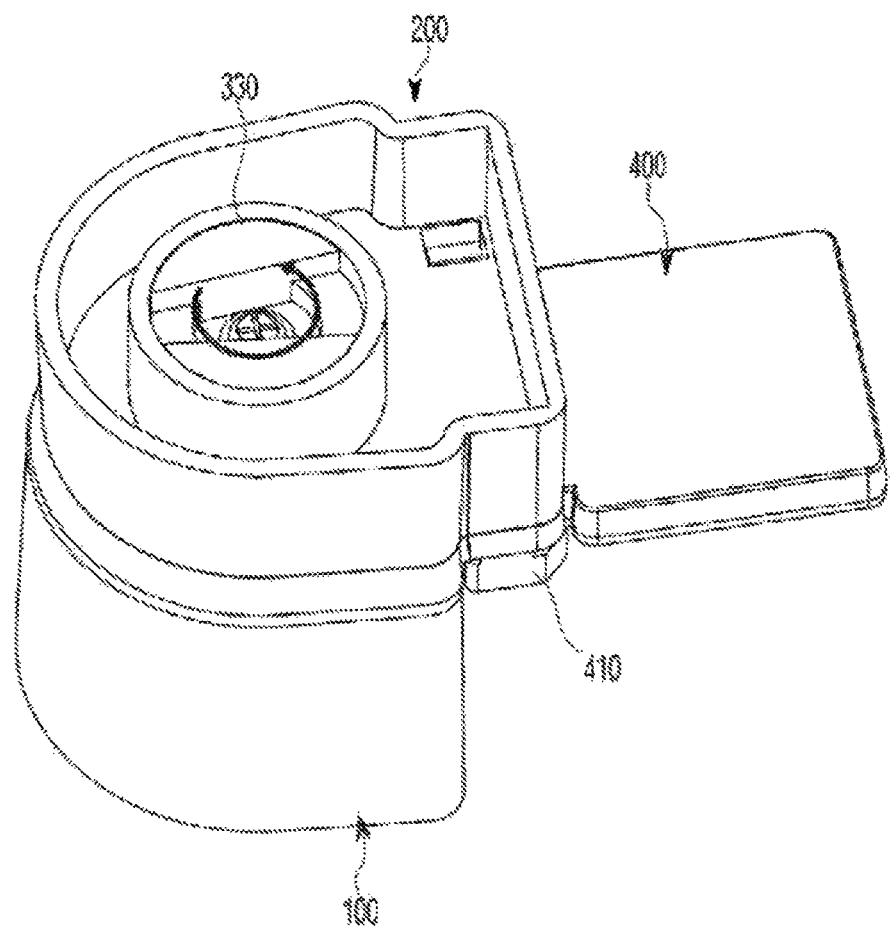

[Fig. 5]
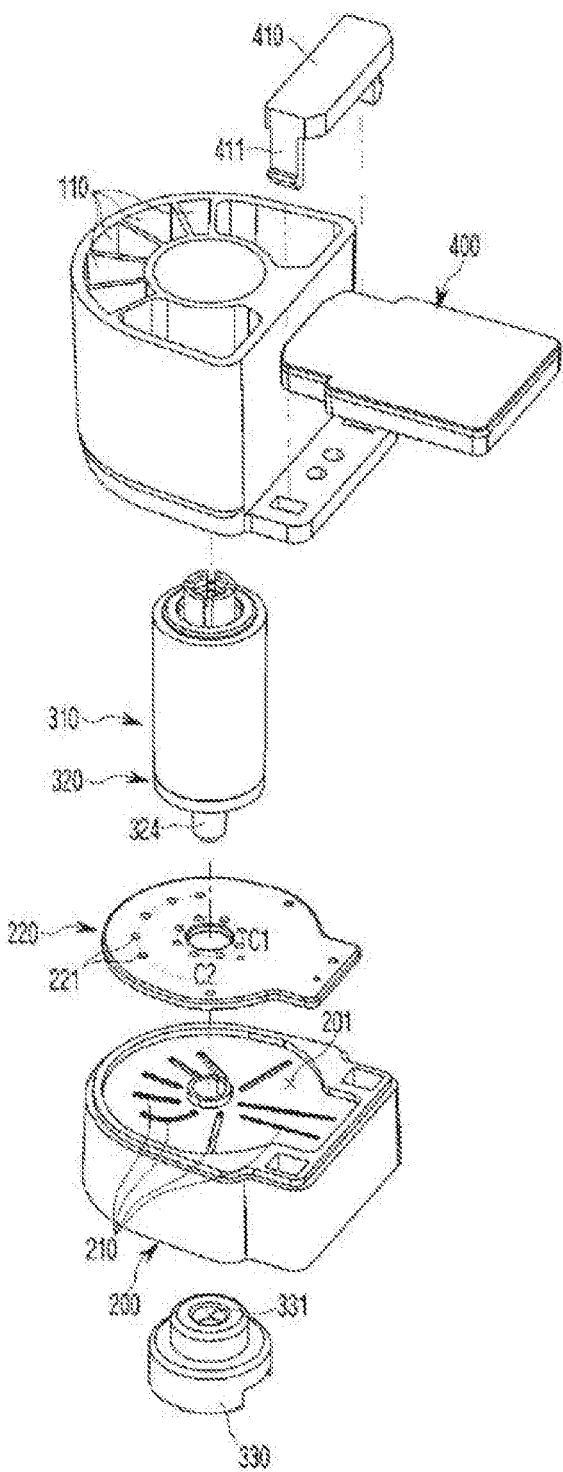

PISTON OF NUCLEIC ACID EXTRACTING CARTRIDGE

TECHNICAL FIELD

The present invention relates to a piston of a cartridge for nucleic acid extraction, and more particularly, to a piston applied to a cartridge capable of separating and purifying nucleic acids from a sample to amplify the nucleic acid.

BACKGROUND ART

In modern times, it has become possible to interpret the cause of disease at the gene level with the development of biotechnology. As a result, the demand for manipulation and biochemical analysis of biological specimens to treat or prevent human diseases is increasing.

Also, in addition to the diagnosis of disease, the technology for extracting and analyzing nucleic acids from samples containing cells or biological specimens is required in various fields such as new drug development, preliminary examination of virus or bacterial infection, and forensic science.

Traditional nucleic acid extractors require each device for each processing process (concentration, purification) and require a long time to move to another device after one processing process is completed.

To address the traditional problem of low detection efficiency with such a long process, U.S. issued U.S. Pat. No. 6,374,684 created multiple bifurcated flows (34,38,42,44) on the piston head, allowing the piston head to rotate and directly inhale reagents in the chamber to mix them in the inner space of the piston.

However, in the case of the cartridge disclosed in U.S. Pat. No. 6,374,684, there is a problem that the structure of the piston is complicated, so that the production and use efficiency of the device may be deteriorated.

DISCLOSURE

Technical Problem

The purpose of this invention is to provide a piston of a cartridge for extracting nucleic acids having a more concise structure.

Technical Solution

In order to achieve the above object, the piston of the cartridge for nucleic acid extraction according to an embodiment of the present invention comprises a cylindrical upper body having a hollow, and a lower body having two ports coupled to one end of the upper body and disposed apart from a certain angle, and a control rod module combined to the other end of the upper body to seal the other end and move up and down along the hollow, and a rotation control combined to the shaft of the lower body to transmit driving force to the lower body.

According to an embodiment of the present invention, the lower body comprises a disk-shaped body, a shaft formed to protrude to the outside from the center of the body, and a liquid port and a filter port disposed at the same distance from the center.

According to an embodiment of the present invention, the filter port comprises a glass fiber filter having various particle sizes, and a support structure for fixing the filter.

According to an embodiment of the present invention, the support structure is formed of a porous plastic material having a certain particle size to prevent the separation of the filter and maintain a constant pressure when discharging the liquid.

According to an embodiment of the present invention, one end of the upper body is formed with a combining structure engaged with the body of the lower body, the combining structure is provided a first hole connected to the liquid port and a second hole connected to the filter port.

According to an embodiment of the present invention, the second holes are formed to have a smaller diameter than the filter port to prevent the support structure and the filter from coming off.

According to an embodiment of the present invention, a groove recessed in the center direction is formed on the outer circumference of the body.

According to an embodiment of the present invention, the rotation control module comprises a combining groove formed to engage the shaft at the center of one surface, and a driving groove formed to engage a drive shaft of the nucleic acid extraction device on the other surface. According to an embodiment of the present invention, the control rod module comprises a coupling region coupled to the control rod of the nucleic acid extraction device, and an adhesion region surrounding the outer circumference of the coupling region and moving in close contact with the inner wall of the upper body.

According to an embodiment of the present invention, the two ports are arranged apart from each other by 18 degrees to 36 degrees.

Effects of the Invention

According to the piston of the cartridge for nucleic acid extraction according to an embodiment of the present invention, the structure of the piston can be simplified by separating the upper body mixing the sample and the reagent and the lower body sucking and discharging the reagent. Through this, the manufacturing and assembly process of the piston can be efficiently performed.

In addition, the lower body of the piston is provided with a liquid port and a filter port that are disposed at a certain angle from each other to allow the reagent suction process and the reagent discharge process to be sequentially performed by rotation of the piston. Through this, it is possible to increase the efficiency of the nucleic acid extraction process.

DESCRIPTION OF DRAWINGS

FIG. 1 is a bottom perspective view of a piston of a cartridge for nucleic acid extraction according to an embodiment of the present invention.

FIG. 2 is a plane view of the piston lower body according to an embodiment of the present invention.

FIG. 3 is a perspective view of a cartridge for nucleic acid extraction apparatus according to an embodiment of the present invention.

FIG. 4 is a bottom perspective view of the cartridge used in the present invention.

FIG. 5 is an exploded view of the cartridge shown in FIG. 2

MODE FOR INVENTION

Hereinafter, the present invention will be described in more detail with reference to the drawings. In this specification, the same or similar reference numerals are assigned to the same or similar configurations in different embodiments, and the description is replaced with the first description. As used herein, a singular expression includes a plural expression unless the context clearly indicates otherwise. In addition, the suffixes "module" and "region" for components used in the following description are given or mixed only considering the ease of writing the specification, and do not have meanings or roles that are distinguished from each other.

FIG. 1 is a bottom perspective view of a piston of a cartridge for nucleic acid extraction according to an embodiment of the present invention, and FIG. 2 is a plane view of a piston lower body according to an embodiment of the present invention.

The piston shown in FIG. 1 is mounted on the cartridge shown in FIGS. 3 to 5 to sequentially inhale and mix samples and reagents disposed in the cartridge chamber to extract nucleic acids.

As shown, the piston (300) may comprise an upper body (310), a lower body (320), a rotation control module (330), a control rod module, and the like.

The upper body (310) forms a cylindrical shape and may include a hollow.

A control rod module that moves up and down along the hollow may be disposed in the hollow of the upper body (310).

The control rod module may comprise a coupling region (301) coupled with a control rod of the nucleic acid extraction device, and an adhesion region (302) surrounding the outer circumference of the coupling region (301) and moving in close contact with the inner wall of the upper body (310).

One end of the upper body (310) may be formed with a combining structure that meshes with the lower body (320), a first hole connected to the liquid port of the lower body (320) and a second hole connected to the filter port of the lower body (320) may be formed. The second hole may be formed to have a smaller diameter than the filter recessing space (323) of the filter port so as to prevent the separation of the support structure and the filter.

The lower body (320) may be coupled to one end of the upper body (310). More specifically, the lower body (320) is fixed in engagement with a combining structure formed at one end of the upper body (310).

The lower body (320) may comprise a disk-shaped body, a shaft (324) formed to protrude from the center of the body to the outside, and a liquid port (321) and a filter port (322) disposed at the same distance from the center of the body. The body may be formed such that the central region (320a) protrudes compared to the outer region (320b). The central region (320a) can be fixed by being inserted into a groove formed on the combining structure of the upper body.

The liquid port (321) is used to inhale, mix, and discharge samples and reagents into the piston, and the filter port (322) can be used to wash the nucleic acid capture filter or separate nucleic acids from the nucleic acid capture filter.

In addition, a groove recessed in the center direction may be formed on the outer periphery of the body of the lower body (320). This groove may serve to remove the vacuum that may occur when moving liquid inside the cartridge.

The liquid port (321) and the filter port (322) are disposed at a certain angle from each other on the same circumference. For example, the filter port (322) and the liquid port (321) may be disposed apart from each other by 18 degrees to 36 degrees. More specifically, the two ports can be arranged to be spaced 22.5 degrees apart. In the case of using a step motor that divides into 16 circuits and performs one rotation, the positions of the liquid port (321) and the filter port (322) may be changed by one drive.

The filter port (322) of the lower body (320) may include a filter recessing space (323), and a filter and a support structure may be disposed in the filter recessing space. As a filter for capturing nucleic acids, a glass fiber filter having various particle sizes can be used, and the supporting structure serves to fix the filter for capturing nucleic acids.

The support structure may be formed of a porous plastic material having a certain particle size so as to prevent the separation of the filter and maintain a constant pressure when discharging the liquid.

The rotation control module (330) is connected to a driving unit of the device and serves as a medium for rotating the piston (300) at a certain angle.

The rotation control module (330) may comprise a combining groove formed to engage the shaft (324) at a central region of one surface, and a driving groove formed to engage a drive shaft of the nucleic acid extraction device on the other surface.

The rotation control module (330) is combined with the piston (300) to position the filter port and the liquid port to the appropriate reagent chamber port position so that various chemical reactions required in the nucleic acid extraction step can be performed within one cartridge.

The liquid port and the filter port are separated by a certain angle, and the rotation control module (330) rotates the ports to a position suitable for each step when extracting nucleic acids.

After inserting a filter necessary for the capture of nucleic acids into the filter port, the lower body (320) is combined with the upper body (310), and then coupled to the first body (100) and the second body (200) to complete the cartridge setting.

Hereinafter, the structure of the cartridge to which the piston described above is mounted will be described in detail with reference to FIGS. 3 to 5.

FIG. 3 is a perspective view of a cartridge used in the present invention, FIG. 4 is a bottom perspective view of the cartridge used in the present invention, FIG. 5 is an exploded view of the cartridge shown in FIG. 3.

FIGS. 3 to 5, the cartridge for nucleic acid extraction may largely be comprised a first body (100), a second body (200), a piston (300), a nucleic acid amplification module (400), and the like.

The first body (100) may be used for the purpose of storing a plurality of reagents.

As illustrated, a plurality of chambers (110) forming compartments separated from each other may be formed in the first body (100). Different reagents or samples are disposed in each chamber (110) and each chamber (110) forms an independent space so that the reagents do not mix with each other.

The second body (200) includes a path through which the reagent or sample stored in the first body (100) moves.

According to an embodiment of the present invention, the second body (200) may have a liquid flow path through which liquid can move and an air flow path through which air can move, and the second body (200) may include a pad (220) disposed on the upper surface to prevent leakage of liquid when combined with the first body (100). When the pad (220) and the cartridge second body (200) are combined, the liquid flow path and the air flow path of the cartridge second body 200 are blocked by the pad (220) to form a space, thereby completing the perfect flow path (210).

The liquid flow path is connected to the first body (100) to provide a space for samples and reagents to move and mix.

The air flow path connects the amplification module and the vacuum control region of the piston (300) to control the vacuum that may occur when the extracted nucleic acid moves to the amplification module, and serves to prevent contamination of the nucleic acid amplification products.

A plurality of holes penetrating the pad (220) up and down may be formed in the pad (220). The liquid and air flow paths under the cartridge are connected to the plurality of reagent chambers (110) located in the cartridge first body (100) through the holes.

The central region of the pad (220) is combined to be in close contact with the bottom surface of the piston lower body (320).

The holes formed in the center of the pad (220) overlap with the filter port or liquid port of the piston lower body (320) when the piston rotates.

More specifically, a plurality of flow paths (210) may be formed on the second body (200). Each flow path (210) does not cross each other and is formed to extend from the center of the second body (200) to the outer region. As shown, some flow paths may have one end disposed on the same circumference and the other end disposed on the same circumference with each other.

The pad (220) may be coupled to the upper region of the second body (200).

The upper region of the second body (200) may be formed with a recessing region (201) recessed toward the bottom, and the pad (220) may be engaged with the recessing region (201) on the upper region of the second body (200).

As the pad (220) is in close contact with the upper surface of the second body (200_, the flow paths (210) may be sealed. The pad (220) may be formed of rubber or synthetic resin having elasticity so that the pad (220) may be more closely adhered to the second body (200).

According to an embodiment of the present invention, the holes are arranged to overlap vertically with the ends of the flow paths (210). In other words, holes formed in the pad (220) may be paired in pairs to be connected through the flow path (210).

The pad (220) may comprise a plurality of holes (221) disposed on the same circumference (C1) in the center and a plurality of holes (221) disposed on the same circumference (C2) in the outer region.

The piston (300) may comprise a piston upper body (310) and a piston lower body (320).

In the upper body (310) of the piston (300), an inner space in which reagents and samples can be mixed is formed, and a control rod module of piston (300) that moves up and down may be disposed in the inner space.

The piston control rod module may include a coupling region (301) coupled with a driving region of the nucleic acid extraction device and an adhesion region (302) moving up and down in close contact with the piston inner space.

The piston lower body (320) is combined with the piston upper body (310) to form one body.

The piston lower body (320) may be combined with the rotation control module (330).

According to the illustrated, the piston upper body (310) is inserted into the hole formed in the central region of the first body (100) and the shaft (324) of the piston lower body (320) is inserted into the hole formed in the central region of the second body (200).

The shaft (324) of the piston lower body (320) is fixed in engagement with the rotation control module (330) combined to the bottom of the second body (200).

The nucleic acid amplification module (400) may be combined with the first body (100) or the second body (200)

The internal flow path (210) may be formed inside the nucleic acid amplification module (400), and one end of the internal flow path (210) may be formed to overlap with at least one of the flow paths (210) formed in the second body (200).

According to one embodiment of the present invention, there may be a fixing member (410) for covering the nucleic acid amplification module (400) and coupling the first body (100) and the second body (200) so that the nucleic acid amplification module (400) is not arbitrarily separated.

The first body (100) may include a plurality of reagent chambers (110), and each chamber (110) is formed to be isolated from each other.

At the bottom of each chamber (110), a port overlapping holes formed in one end of the flow path (210) or the pad (220) is formed. Ports may be formed to have different radii depending on the purpose of the chamber (110).

Each reagent chamber (110) includes a single reagent chamber liquid port. Each reagent chamber liquid port is connected to the liquid flow path at the bottom of the cartridge through the liquid port connection hole of the rubber pad (220). A separate sample chamber and a master mix bead chamber (111) are combined to the sample chamber port and the master mix bead chamber port, respectively.

Sample chamber ports may be disposed on the same circumference, and the master mix bead chamber ports may be placed on different circumferences.

The sample chamber may include several dry beads required for sample extraction, and the master mix bead chamber may include several dry beads required for nucleic acid amplification.

The sample chamber and the master mix bead chamber are respectively connected to the sample chamber port and the master mix bead chamber port, and each port is connected to a hole formed in the pad and a flow path of the cartridge second body (200) to form a structure in which the liquid can move.

According to the piston of the nucleic acid extraction cartridge described above, the structure of the piston can be simplified by separating the upper body mixing the sample and reagent and the lower body sucking and discharging the reagent. Through this, the manufacturing and assembly process of the piston can be efficiently performed.

In addition, the lower body of the piston is provided with a liquid port and a filter port that are disposed at a certain angle from each other to allow the reagent suction process and the reagent discharge process to be sequentially performed by rotation of the piston. Through this, it is possible to increase the efficiency of the nucleic acid extraction process.

The cartridge for nucleic acid extraction described above is not limited to the configuration and method of the above-described embodiments, but the above embodiments may be configured by selectively combining all or part of each embodiment so that various modifications can be made.

The invention claimed is:

1. A piston of a nucleic acid extraction cartridge for extracting nucleic acids by sequentially sucking and mixing samples and reagents disposed in the cartridge, wherein the cartridge comprises:

a first body including a plurality of chambers having a port formed at a bottom of the first body, a second body coupled to a lower portion of the first body;

a pad which is disposed on an upper surface of the second body and having a plurality of holes penetrating therethrough and in which a plurality of holes disposed along a same circumference at a center of the pad and a plurality of holes disposed along a same circumference at an outer region of the pad are formed through the pad, and a plurality of flow paths which are formed on the upper surface of the second body to extend from a center of the second body to an outer portion of the second body and in which an end of the plurality of flow paths overlaps with the plurality of holes on the same circumference in the center of the pad and another end of the plurality of flow paths overlaps with the plurality of holes on the same circumference in the outer region of the pad and also with the port of the plurality of chambers, wherein the piston comprises:

a cylindrical upper body having a hollow;

a lower body having two ports coupled to one end of the cylindrical upper body and communicated with the hollow, and the two ports disposed at a certain angle apart from each other on a same circumference;

a control rod module combined to the other end of the cylindrical upper body to seal the other end and move up and down along the hollow; and a rotation control module that is combined to a shaft of the lower body to transmit a driving force to the lower body, wherein the port of the lower body overlaps with any one of the plurality of holes disposed on the same circumference in the center of the pad when the piston rotates.

2. The piston of a nucleic acid extraction cartridge according to claim 1, wherein said lower body is comprising:

a disk-shaped body;

the shaft formed to protrude from a center of the disk-shaped body to an outside; and a liquid port and a filter port disposed at the same distance from the center.

3. The piston of a nucleic acid extraction cartridge according to claim 2, wherein said filter port comprises a glass fiber filter having various particle sizes; and a support structure for fixing the filter.

4. The piston of a nucleic acid extraction cartridge according to claim 3, wherein at one end of the upper body, a combining structure that is engaged with the body of the lower body is formed, and the combining structure is provided with a first hole connected to the liquid port and a second hole connected to the filter port.

5. The piston of a nucleic acid extraction cartridge according to claim 4, wherein the second hole is formed to have a smaller diameter than the filter port to prevent separation of the support structure and the glass fiber filter.

6. The piston of a nucleic acid extraction cartridge according to claim 2, wherein a groove recessed in a center direction is formed on an outer circumference of the disk-shaped body.

7. The piston of a nucleic acid extraction cartridge according to claim 2, wherein said rotation control module comprises a coupling groove formed to engage the shaft at the center of one surface; and a driving groove formed on the other surface to be engaged with a driving shaft of the nucleic acid extraction device.

8. The piston of a nucleic acid extraction cartridge according to claim 1, wherein said control rod module comprises a coupling region is coupled to a control rod of the nucleic acid extraction device; and an adhesive region surrounding an outer circumference of the coupling region and moving in close contact with the inner wall of the upper body.

9. The piston of a nucleic acid extraction cartridge according to claim 1, wherein said two ports are arranged 18 to 36 degrees apart from each other.

\* \* \* \* \*